United States Patent [19]

Strauss et al.

[11] Patent Number: 5,895,759
[45] Date of Patent: *Apr. 20, 1999

[54] VECTOR FOR GENE TRANSFER IN LIVER CELLS

[75] Inventors: Michael Strauss; Volker Sandig; Christian Hofmann, all of Berlin, Germany

[73] Assignee: Max-Planck Gesellschaft zur Förderung der Wissenschaften e.V., Germany

[*] Notice: This patent issued on a continued prosecution application filed under 37 CFR 1.53(d), and is subject to the twenty year patent term provisions of 35 U.S.C. 154(a)(2).

[21] Appl. No.: 08/697,998

[22] Filed: Sep. 3, 1996

Related U.S. Application Data

[63] Continuation of application No. 08/300,714, Sep. 2, 1994, abandoned.

[30] Foreign Application Priority Data

Sep. 3, 1993 [DE] Germany ............... 43 29 811
Nov. 19, 1993 [DE] Germany ............... 43 39 922

[51] Int. Cl.$^6$ ............ C12N 15/00; A01N 37/18; A01N 43/04; C07K 1/00
[52] U.S. Cl. ............ 435/320.1; 514/2; 514/44; 530/350; 530/402
[58] Field of Search ............ 435/320.1, 172.3; 424/93.1, 93.21; 514/44, 2; 530/350, 402

[56] References Cited

U.S. PATENT DOCUMENTS 5,166,320 11/1992 Wu et al. ............... 530/395

FOREIGN PATENT DOCUMENTS 4339922 9/1993 Germany .
9506745 3/1995 WIPO .

OTHER PUBLICATIONS

Gutierrez et al. 1992. The Lancet 339:715–719.
Ledley et al. 1991. Human Gene Therapy 2:77–83
Wu et al. 1991. Biotherapy 3:87–95.
Pontisso et al. 1989. J. Virol. 63(5):1981–1988.
Antonucci et al. 1989. J. Virol. 63(2):579–583.
Bottger et al. 1988. Biochimica et Biophysica Acta 950:221–228.
Yamaizumi et al. 1978. Nature 273:782–784.
Smirnov et al. 1986. Proc. Natl. Acad. Sci. USA. 83:6603–6607.
Peeters et al. 1989. J. Immunol. Methods 120:133–143.
Songsivilai et al. 1990. Clin Exp. Immunol. 79:315–321.
Webb, ed. Enzyme Nomenclature 1984. Academic Press, Inc., Orlando., pp. 220–230.
Tessier, D.C., et al.; Enhanced Secretion from Insect Cells of a Foreign Protein Fused to the Honeybee Melittin Signal Peptide; Genetic Engineering Section, National Research Council of Canada, Montreal Quebec. Gene. Feb. 15, 1991; 98(2): 177–83; Bibliothek Max–Delbrück–Centrum.
Orkin et al. (referred to as NIH panel report) Report and recommendations of the panel to assess the NIH investment in research on gene therapy. Distributed by the National Institutes of Health, Bethesda, MD., Dec. 7, 1996.

Primary Examiner—Deborah Crouch
Assistant Examiner—Deborah J. R. Clark

[57] ABSTRACT

A tissue-specific, suitably liver specific vector for gene therapy of a diseased host, wherein a therapeutic gene is coupled to a promoter chemically, enzymatically, or over an antibody, packaged in a polypeptide coat, and coupled to a component of a preselected virus of the tissue to be treated, and when the tissue is liver tissue, then the virus is hepatitis B virus.

3 Claims, No Drawings

VECTOR FOR GENE TRANSFER IN LIVER CELLS

This is a continuation of patent application Ser. No. 08/300,714, filed on Sep. 2, 1994, now abandoned.

FIELD OF THE INVENTION

The invention relates to a tissue-specific vector for gene therapy, suitably a vector for liver-specific gene therapy. The vector is particularly useful in medicine and genetic engineering.

BACKGROUND OF THE INVENTION

Numerous methods and vectors for gene therapy have been developed in recent years. A survey is given by Mulligan in Science, 1993, pp. 260, 926. Many vectors are favored for gene therapy, particularly those, which are derived from retroviruses or adenoviruses. Both types of virus vectors are relatively broadly useful. Retroviral vectors are generally effective only in proliferating cells. Adenoviruses also infect nondividing cells. Although both types of vectors are suitable for gene transfer in vitro into liver cells (hepatocytes), but they can hardly be considered for use in in vivo gene therapy in humans. Although a partial liver resection is necessary to stimulate cell division (regeneration) in the application of retroviral vectors, the adenoviral gene transfer is not very stable, because no gene integration into the genome takes place.

Alternative vectors with potential applicability for gene transfer to liver cells are based on liposomes, or are also based on multicomponent particles with protein domains, which bind specifically to receptors of the live cell, such as the asialoglycoprotein receptor, and can be taken up in the cell due to receptor internalization. These were surveyed by Versland et al. in 1992 Seminars in Liver Disease 12, 332. An important disadvantage of these vectors is the endocytotic pathway, which leads to a degration of a large portion of the vectors and their DNA in the endosomes, so that only small amounts of functional DNA can reach the cell nucleus.

A solution to this problem was found for in vitro application, but that is not useful for in vivo use in patients. The principle is based on the simultaneous infection of the target cells with adenovirus, which leads to a disruption of the endosomes and a release of vector (DNA) as described by Curiel, D. T., Agrawal, S., Wagner, E. and Cotten, M. 1991, PNAS 88, 8850-8854.

DESCRIPTION OF THE INVENTION

The object of the invention is the construction of a vector which targets tissue cells, suitably liver cells, highly specifically in vivo, is effectively taken up by the cells, and can direct the therapeutic genes into the cell nucleus. The vector is useful for gene therapy in various animal hosts. Although the present invention is described principally with reference to the liver-specificity of the vector, it is to be understood that the present invention encompasses animal tissue specificity more generally.

The present invention comprises a tissue specific vector for gene therapy, suitably a liver-specific vector, for gene therapy of an animal host, wherein a therapeutic gene is fused to the tissue specific promoter, is packaged in a polypeptide coat, and is coupled chemically, suitably enzymatically, or by antibodies, to components, suitably protein domains, of a component of a specific virus of the tissue to be treated; and if the tissue is liver tissue, then to hepatitis B virus (HBV). The cDNA of a gene is used as therapeutic gene to treat a disease caused by a missing or mutated gene.

An example of such genes is the LDL receptor gene, the absence of which causes the most frequently occurring metabolic disease of the liver, the familial hypercholesterolemia. Another example is the alpha-1-antitrypsin gene.

Liver-specific promoters can be used, suitably promoters/enhancers of the HBV, such as the combinations of core promoter/enhancer II. In addition to their specificity, they are also sufficiently small to be easily incorporated in an expression vector. Promoters of liver-specific genes, such as albumin, phosphenol pyruvate carboxykinase (PEPCK) or ornithine transcarbamylase (OTC) can also be considered for the construction of the vector of the present invention.

The polypeptide coat that is used for the packaging is suitably a chromosomal protein, such as purified high mobility group protein 1 (HMG1). Other DNA-binding proteins, such as protamines, or hepatitis core protein, are also suitable. The core protein is particularly suitable because, in addition to its DNA binding and DNA condensation capabilities it is a natural component of the HBV and therefore favors incorporation in the virus coat.

The polypeptide coat of the present invention can also be prepared from polyamino acids of one type of basic amino acids. Particularly suitably are poly-L-lysine, and poly-L-ornithine.

Naturally occurring HBV particles that can be used as coupled component pursuant to the present invention, can be isolated from virus-producing cells. For reasons of safety, however, pre-S1/S (small) protein domain on the hepatitis surface protein is suitably produced by genetic engineering. Such particles, which are free of nucleic acids, as seen from the outer surface, represent a complete virus coat. Thus, the resulting vector has a high degree of homology with natural HBV and can therefore reconstruct the infection mechanism.

Instead of using complete virus coat proteins, the present invention can also be realized with liposomes as transport vehicles. For this purpose, the surface of the employed liposomes is modified by pre-S1/S protein so that absorption is possible thru hepatitis B-specific mechanisms.

The vectors can be prepared by chemically enzymatically, or through antibodies coupling the packaged gene, on a component of the HBV Suitably, the gene, packaged in HMG1, can be coupled covalently to the pre-S1and S proteins of the HBV by the transglutaminase reaction such as transaminase. Suitably selectively a bifunctional linker (SPDP), or a bispecific antibody is employed.

The vector of the present invention enables the introduction of a desired gene into the liver of a patient, and optimally configures its path to the site at which it functions. This is accomplished, for example, due to the fact that the vector is prepared and administered to the bloodstream of a patient, suitably into the portal vein. The present invention enables significant treatment of genetic diseases of the liver.

The invention is described in further greater detail by the following illustrative embodiments thereof.

1. Expression of HBV coat proteins in insect cells

The coat of the HBV virus contains three proteins that are translation products of an open reading frame in the HBV genome with different initiation sites. The large coat protein (L: P39, GP42) contains the pre-S1, pre-S2 and S domains, the medium-sized coat protein (M: P33, GP36) consists of pre-S2 and S domains, and the small coat protein (S: P24, GP27) contains only the S domains.

The genes of the small (S) and large (L) HBV coat proteins are obtained by amplification from the genome of the HBV (subtype ayw). Different variations are drawn up for the L gene, to facilitate the secretion of the protein. They code for an N-terminaly deleted L protein (deletion of the 1–6 amino acids), an L protein, the myristillation site of which is mutated (amino acid 2 gly→ala) or a fusion with the mellitin signal sequence.

All genes were cloned individually in the baculovirus transfer vector PVL941 and are under the control of the polyhedrin promoter. Subsequently, a DNA fragment, of the polyhedrin promoter and the S gene is inserted in all vectors, which contain variations of the L gene, in such a way that both expression units are present in the same orientation and are flanked by baculovirus sequences.

The recombinant plasmids and baculovirus DNA (BaculoGold) are cotransfected with lipofectin in Spodoptera frugiperda cells (Sf9). Recombinant baculoviruses are produced due to homologous recombination between plasmid and virus DNA, which express the HBV coat proteins under the control of the polyhedrin promoter in infected Sf9 cells. The synthesis of these proteins is demonstrated by the Western Blot. It is electron microscopically shown that the coat proteins associate into particles.

After repeatedly subjecting the viruses to passage through Sf9 cells, Spinner cultures ($10^9$ Sf9 cells) are infected and, the cells are harvested 72 hours post-infection by sedimentation, and are ultrasonically lysed. The coat particles are purified after removal of the membranes by sedimentation, either by centrifugation in the CsCl density gradient or by affinity chromatography. S-specific monoclonal antibodies are used for the latter.

2. Expression and purification of HMG1

The gene of the non-histone protein HMG1 of the rat is taken from the vector for bacterial expression pT7RNHMG1, as described by Bianchi, E., in Gene, vol. 104 (1991) pp. 271–275 and is cloned in the baculovirus transfer vector PVL941.

Recombinant baculoviruses are produced by the method described for the HBV gene. The expression was confirmed by Coomassy staining of the proteins after SDS polyacrylamide gel electrophoresis.

A cell lysate is prepared by sonication, to purify rat HMG1 from infected Sf9 cells, the membranes are separated by sedimentation and the lysate is precipitated with 2% trichloroacetic acid (TCA). The supernatant is subsequently subjected to an acetone precipitation in an acidic medium. The resulting precipitate is dissolved and fractionated by ion exchange chromatography on a mono Q column in a salt gradient. The fraction is eluted at 1.7M NaCl, and contains electrophoretically pure HMG1.

3. Preparation of DNA-HMG1 complexes.

Plasmid DNA of form 3 is bound and condensed sequence-independently by HMG1 by the method of Boettger et al. in Biochim. Biophys. Acta Vol. 950 (1988) pp. 221–228. The DNA-protein complexes are formed by the stepwise addition of a 20-fold excess by weight of HMG1 to a 50 μg/mL DNA solution in a 10 mM tris/HCl buffer at a pH of 8 and containing 150 mM of NaCl. DNA binding and condensation were demonstrated by gel retardation and sedimentation in the sucrose gradient.

4. Binding of DNA-HMG1 complexes to HBV particles

HBV coat proteins were cross linked by means of transglutaminase, covalently with HMG1. In this reaction, ε-amino groups of the lysine in the HMG molecule appear as acyl acceptor, and the -carboxamide groups of the glutamine groups in the HBV L and S protein appear as acyl donor.

The reaction is carried out for 1 hour at 37° C. in 150 mM NaCl, 10 mM $CaCl_2$, and 20 mM tris/HCl buffer of pH 8.0, with 0.5 units of guinea pig transglutaminase at a weight ratio of HMG1:HBVL+S of 10:1.

5. Infection of primary human hepatocytes with the gene transfer vector

A confluent monolayer culture of human hepatocytes is infected five days after it is prepared, for 12 hours with the transfer vector. The plasmid pBAG, disclosed in Proc. Natl. Acad. Sci. Vol. 84 (1987), pp. 156–160, which contains the gene of β-galactosidase from *E. coli* under the control of a viral retroviral LTR, is packaged in the vector. The gene transfer is confirmed 48 hours after infection by the in situ enzyme test for β-galactosidase.

We claim:

1. A vector comprising:

A) a liver specific gene operatively linked to a promoter, wherein said promoter is selected from the group consisting of
   1) a hepatitis B virus (HBV) promoter, and
   2) both an HBV promoter and enhancer; wherein said gene/promoter linkage is packaged in B) a polypeptide coat of high mobility group protein 1 (HMG1), to form a coated gene/promoter package, said package being crosslinked to C) a combination consisting of pre-S 1 and S proteins of HBV.

2. A process for producing the vector of claim 1, wherein the coated gene/promoter package is chemically or enzymatically crosslinked to said combination of pre-S1 and S proteins.

3. The process of claim 2 wherein said crosslinking is carried out with a transaminase.

* * * * *